United States Patent
Hawkes et al.

(10) Patent No.: US 10,893,352 B2
(45) Date of Patent: Jan. 12, 2021

(54) PROGRAMMABLE INTERACTIVE STEREO HEADPHONES WITH TAP FUNCTIONALITY AND NETWORK CONNECTIVITY

(71) Applicants: Matthew Hawkes, South Jordan, UT (US); Spencer Lifferth, Layton, UT (US); Denarius Motes, Woodland Hills, CA (US); David Tucker, Salt Lake City, UT (US)

(72) Inventors: Matthew Hawkes, South Jordan, UT (US); Spencer Lifferth, Layton, UT (US); Denarius Motes, Woodland Hills, CA (US); David Tucker, Salt Lake City, UT (US)

( * ) Notice: Subject to any disclaimer, the term of this patent is extended or adjusted under 35 U.S.C. 154(b) by 0 days.

(21) Appl. No.: 15/365,719

(22) Filed: Nov. 30, 2016

(65) Prior Publication Data
US 2018/0132027 A1    May 10, 2018

Related U.S. Application Data

(63) Continuation-in-part of application No. 15/246,521, filed on Aug. 24, 2016.

(51) Int. Cl.
| | |
|---|---|
| *H04R 1/10* | (2006.01) |
| *H04R 25/00* | (2006.01) |
| *G06F 3/16* | (2006.01) |
| *G06F 3/0488* | (2013.01) |
| *G06F 3/0487* | (2013.01) |
| *H04R 5/033* | (2006.01) |

(Continued)

(52) U.S. Cl.
CPC .......... *H04R 1/1041* (2013.01); *A61B 5/123* (2013.01); *G06F 3/04847* (2013.01); *G06F 3/04883* (2013.01); *G06F 3/165* (2013.01); *A61B 5/6803* (2013.01); *A61B 5/6898* (2013.01); *H04R 1/105* (2013.01); *H04R 1/1008* (2013.01); *H04R 5/0335* (2013.01); *H04R 25/70* (2013.01); *H04R 2201/103* (2013.01); *H04R 2225/55* (2013.01); *H04R 2420/07* (2013.01); *H04R 2420/09* (2013.01)

(58) Field of Classification Search
CPC .... H04R 1/1041; H04R 1/1008; H04R 1/105; H04R 5/0335; H04R 2420/07; G06F 3/165; A61B 5/123
See application file for complete search history.

(56) References Cited

U.S. PATENT DOCUMENTS

| | | | |
|---|---|---|---|
| 9,706,304 B1 * | 7/2017 | Kelso | H04R 3/04 |
| 2002/0003889 A1 * | 1/2002 | Fischer | H04R 1/1041 381/370 |

(Continued)

*Primary Examiner* — Sonia L Gay
(74) *Attorney, Agent, or Firm* — Steven Rinehart

(57) ABSTRACT

Headphones are provided having virtual controls displayed on a circular touch screen and integrated memory, the headphones comprising a arcuate headband, a receiver, a transmitter, and computer-readable memory. The headphones are adapted to interact with a wearer through the virtual controls, permitting a wearer to share media wirelessly, assign playback settings, and to accept wireless input from a remote data processing (DPD) device. The headphones may perform a hearing screen test to determine using tones at predetermined frequencies then to amplify frequencies at which a user experiences hearing loss during playback.

15 Claims, 9 Drawing Sheets

(51) Int. Cl.
*A61B 5/12* (2006.01)
*A61B 5/00* (2006.01)
*G06F 3/0484* (2013.01)

(56) References Cited

U.S. PATENT DOCUMENTS

| | | | |
|---|---|---|---|
| 2008/0048878 A1* | 2/2008 | Boillot | G06F 3/017 340/686.1 |
| 2009/0315708 A1* | 12/2009 | Walley | H03G 7/08 340/540 |
| 2014/0036127 A1* | 2/2014 | Pong | H04R 1/028 348/333.01 |
| 2014/0075311 A1* | 3/2014 | Boettcher | G06F 3/017 715/716 |
| 2014/0119554 A1* | 5/2014 | Chan | H04R 1/1091 381/74 |
| 2016/0050476 A1* | 2/2016 | Patil | G06F 3/04847 715/728 |
| 2016/0162252 A1* | 6/2016 | Di Censo | G06F 3/165 700/94 |
| 2016/0216943 A1* | 7/2016 | Welti | G06F 3/167 |
| 2017/0046120 A1* | 2/2017 | Jeffery | G06F 3/165 |
| 2017/0329510 A1* | 11/2017 | Gorlich | G06F 3/04883 |
| 2018/0098720 A1* | 4/2018 | Raz | A61B 5/123 |

\* cited by examiner

Touch display 202

PROGRAMMABLE INTERACTIVE STEREO HEADPHONES WITH TAP FUNCTIONALITY AND NETWORK CONNECTIVITY

CROSS-REFERENCE TO OTHER APPLICATIONS

This patent application claims priority to, and incorporates, U.S. provisional patent application Ser. No. 15/246,621 entitled "Interactive Stereo Headphones with Virtual Controls and Integrated Memory" filed on Aug. 24, 2016 for Spencer Lifferth.

BACKGROUND OF THE INVENTION

Field of the Invention

This invention relates to headphones, and more particularly relates to interactive stereo headphones with integrated memory and virtual controls.

Description of the Related Art

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Headphones are well-known in the art, and generally include a pair of small loudspeakers that are designed to be held in place close to a user's ears. Headphones typically either have wires for connection to a signal source such as an audio amplifier, radio, CD player, portable media player or mobile phone, or have a wireless receiver. Typically, headphones in the art emit sound that is perceptible by humans at frequencies from about 20 Hz to 20,000 Hz.

Headphones heretofore devised and utilized are known to consist of an adjustable headband and a pair of earpieces coupled to the headband. Each of the earpieces has an open inner face which defines a cavity in the respective earpiece. Each earpiece may also have a generally circular shaped fabric covered shield covering the open inner face of the respective earpiece. The inner face of each of the earpieces has a center extent extending into the cavity of the respective earpiece. The center extent has a plurality of side faces each having at least one speaker mounted thereto.

Traditional headphones including cumbersome wires have not traditionally included separate power supplies. Traditional headphones have not typically included amplifiers, and serve only to emit sounds through integrated speakers rather than to interact with a user or provide playback functionality. Audio recordings and playback of audio recording is traditionally handled by a data processing device (DPD) in logical connectivity with the headphones, while the headphones themselves lack this ability.

Additionally traditional headphones are adapted only to provide sound discretely to a listener, and do not include means of wirelessly receiving or transmitting sound or other media.

In these respects, interactive headphones according to the present invention substantially depart from the conventional concepts and designs of the prior art, and in so doing provide an apparatus for enhancing a wearer's listening experience by providing integrated playback function, integrated memory, and integrated playback controls.

In view of the foregoing, it is clear that these traditional headphones are not optimal and leave room for more optimal approaches. There is a need in the art for interactive headphones with integrated controls and memory. It is therefore desirable that such an apparatus and system be provided.

SUMMARY OF THE INVENTION

From the foregoing discussion, it should be apparent that a need exists for a interactive headphones with virtual controls and integrated memory. Beneficially, such an apparatus would overcome many of the difficulties with prior art by providing a single apparatus with integrated power supply, audio files and playback functionality.

The present invention has been developed in response to the present state of the art, and in particular, in response to the safety problems and needs in the art that have not yet been fully solved by currently available aparati. Accordingly, the present invention has been developed to provide a programmable interactive stereo headphones with tap functionality and network functionality, the headphones comprising: an arcuate headband adapted for contouring a wearer's head, the arcuate headband affixed to two earphones; two earphones, each earphone comprising a speaker; a circular touch screen recessed into an exterior outer surface of the arcuate headband for receiving tactile input from a wearer; a battery; persisten computer-readable memory; a control module comprising a processor, the control module configured to display virtual controls on the touch display; a receiving module configured to receive tactile input from a user.

The virtual controls may be manipulable to start, stop, fastforward and rewind playback of an audio file in computer readable memory. The headphones may be adapted to share media wirelessly with one or more separate headphones using Bluetooth® technology.

The headphones may be adapted to test hearing loss by playing a series of tones of predetermined escalating frequencies one at a time in a single earphone; to accept input from a user in response to the user hearing the tones; to create a profile of the wearer's hearing sensitivity; and to save the profile in the computer readable memory; and to amplify tones at which a user experiences hearing loss during media playback.

The virtual controls may be manipulable, in some embodiments, using taping from a user to start, stop, fastforward and rewind playback of an audio file in computer readable memory.

The headphones may further comprise a plurality of depressible buttons for raising and lower a volume of sound emanating from the speakers. The control module may be configurable by a user to set a maximum volume decibel level for each respective speaker, the maximum volume decibel level stored in the computer readable memory.

The control module may limit sounds emitting from each speaker to a volume less than the maximum volume decibel level exclusively associated with said speaker. The touch screen may be adapted to fast forward playback of an audio file in computer-readable memory in response to sensing a wearer's engagement of the touch screen with a finger in a clockwise direction.

The touch screen may be adapted to rewind playback of an audio file in computer-readable memory in response to sensing a wearer's engagement of the touch screen with a finger in a counterclockwise direction. The touch screen may be adapted to stop forward playback of an audio file in computer-readable memory in response to sensing a wearer's taping the touch screen with a finger.

The touch screen is adapted, in various embodiments, to return to a main menu in response to sensing a wearer's taping the touch screen with two fingers. The touch screen may be adapted to return to a main menu in response to sensing a wearer's taping the touch screen with two fingers.

The headphones may further comprise a wireless receiver, the headphones adapted to receive wireless input via the wireless receiver transmitted from a tablet computer, the wireless input changing playback settings on the headphones. The output of the speakers may be limited to 85 decibels.

The touch screen may be configured by the wearer to display a still or video images as specified by the user. In some embodiments, the image displayed by selected by the user. For instance, the logo of user/wearer's favorite sports team, such as BYU or the Utah Jazz, could be displaying during playback of a sporting event.

In alternative embodiments, the image may exclusively associated with audio being played on the headphones. Alternatively, the image or video displayed could be one not associated with playback but selected by the user/wearer. The audio file being played back on the headphones may be transmitted wireless to a second pair of headphones inconnected with the headphones via a LAN. The headphones may further comprise a forward facing camera.

A second programmable interactive stereo headphones with tap functionality and network functionality are also provided, the headphones comprising: an arcuate headband adapted for contouring a wearer's head, the arcuate headband affixed to two earphones; two earphones, each earphone comprising a speaker; a circular touch screen recessed into an exterior outer surface of the arcuate headband for receiving tactile input from a wearer; a battery; persistent computer-readable memory; a control module comprising a processor, the control module configured to display virtual controls on the touch display; a receiving module configured to receive tactile input from a user; wherein the virtual controls are manipulable to start, stop, fastforward and rewind playback of an audio file in computer readable memory; wherein the headphone are adapted to share media wirelessly with one or more separate headphones using Bluetooth® technology; wherein the headphone are adapted to test hearing loss by playing a series of tones of predetermined escalating frequencies one at a time, to accept input from a user in response to the user hearing the tones, and to amplify tones at which a user experiences hearing loss during media playback.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to convey a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
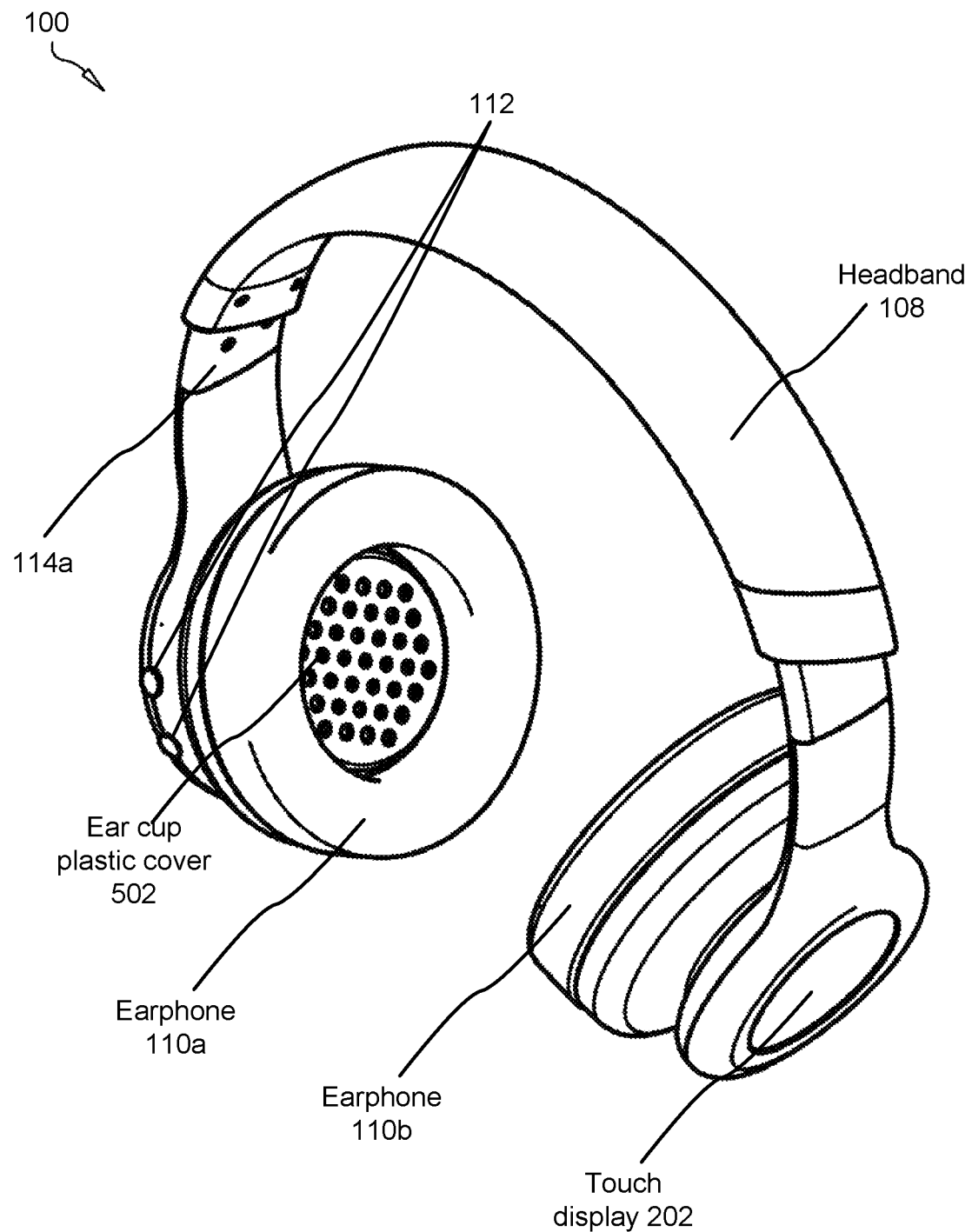
FIG. 1 is a side forward perspective view of programmable interactive stereo headphones with tap controls and network connectivity in accordance with the present invention.

FIG. 1 is a forward perspective view of programmable interactive headphones 100 with virtual controls and integrated memory in accordance with the present invention. The headphones 100 comprise an arcuate headband 108, a main inner body 114a, a main inner body 114b, an earpiece 110a, an earpiece 110b, and two depressible buttons 112a-b.

The arcuate headband 108 comprises a tubular bowed component adapted to conform to the exterior top surface of a wearer's skull. In various embodiments, the arcuate headband is flexible facilitating additional adjustment.

The headband 108 defines, in the shown embodiment, two hollow interior recesses in which a main inner body 114 travels. The headband 108 has two open ends for permitting the main inner bodies 114 to be inserted and adjusted slidably related to the headband 108. These interior recesses receive a male end of the main inner bodies 114.

In various embodiments, the arcuate headband 108 and the main inner bodies 114 are formed from polymeric, organic, or metallic materials, including steel, nylon and leather. The arcuate headband 108 may be formed as a single integrated piece, or may comprise a plurality of layered components which snap or are otherwise affixed together using meanings known to those of skill in the art.

Likewise, the main inner bodies 114 may also be formed as a single integrated piece, or be formed from a plurality of components, usually mold injected, which are affixed together. The main inner bodies 114 protrude downwardly on the longitudinal axis and provide affixation points for the earpieces 110.

The depressible buttons 112a-b may comprise volume controls which are adapted to raise or lower volume of sound emitting or emanating from speakers within the earpieces 110a-b. In various embodiments, the depressible buttons 112 raise or lower resistance to electrical current flowing to the speakers.

The headphones 100 may comprise a camera 116 as shown. In the shown embodiment, the camera is forward facing enabling a wearer to film video of scenes in front of the headphones 100 and record these video files in computer readable memory. In various embodiments, the headphones 100 may be set or configured by the wearer to transmit these video files to a remote data processing device (DPD) including a second pair of headphones 100 and/or a tablet computer, smart phone, desktop, server and the like.

In various embodiments, the camera 116 is housed with an aperture or recess on the exterior of the main inner body 114a or main inner body 114b. In other embodiments, the headphones 100 comprise a plurality of cameras adapted for use in different lighting and environmental conditions.

The headphones 100 also comprises persistent computer-readable memory. The memory may comprise a memory card, and is well-known to those of skill in the art. The memory may be insertable and removable from a positioning slot defined by the main inner body 114. In various embodiments, the audio recordings are stored in the memory for playback by the headphones 100. The audio recordings may be in MP3, WAV, or other formats known to those of skill in the art. In various embodiments, other types of computer readable media are stored in the memory, including video and images in formats known to those of skill in the art, including JPG, SNP, and MP4.

The touch screen 202 is circular in the shown embodiment to facilitate provision of circular virtual controls and to increase resemblance of the touch display 202 to a vinyl record when a vinyl record is displayed on the touch display 202. In the shown embodiment, a manufacturer logo is presently displayed on the touch display 202.

A depressible power button adapted to activate, power on, and boot up the headphones 100 may be disposed beneath the touch screen 202 on the main inner body 114.

The concave housing 306 may be formed from polymeric, metallic, or metal alloys. The concave housing 306 defines a hollow interior recess for receiving and housing a number of components, including a speaker, a middle balance ring, an aluminum ear cup, an ear cup plastic liner, and an ear cup plastic cover.

Figure 2A:
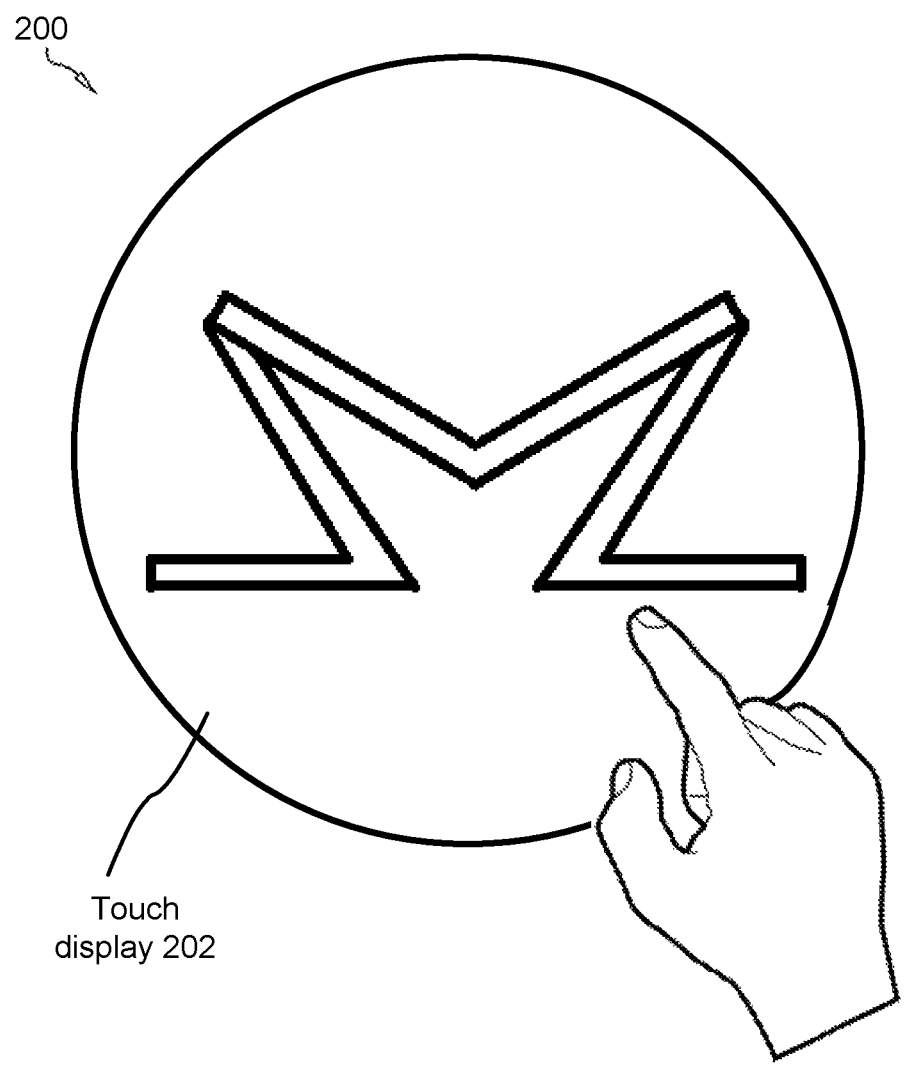
FIG. 2A is a side perspective view of a touch screen of programmable interactive stereo headphones with tap controls and network connectivity in accordance with the present invention.

FIG. 2A is a side perspective view of a touch screen of programmable interactive stereo headphones 200 with tap controls and network connectivity in accordance with the present invention.

The headphones 200 are programmable using an interface on the touch display 202 with the setting saved in computer readable memory. The setting on the headphones which are configurable may comprise: volume setting for each earphone 110, bass and treble settings for each earphone 110, wireless network settings, including password and network keys, and replay settings.

The touch display 202 in the shown embodiment comprises resistive touchscreen, including an input device layered an electronic visual display, such as an LCD screen or plasma screen. The touch display 202 may comprise several layers including two or more electrically-resistive layers separate by a compressible insulator. The the outer layer is pressed against the inner layer by a wearer of the headphones.

The touch display 202 may also comprise a capacitive touch screen, a surface acoustic wave touch screen, an infrared grid, or other type of touchscreen commonly known to those of skill in the art. The touch display 202 is a high resolution digital display which may comprise a plurality of florescent lamps behind a diffuser.

The headphones 200 comprises means for relaying and receiving electrical signals enabling device-to-device communication (meaning wireless transmission of media between headphones 100). The headphones 100 may be configured to make use of the Bluetooth® protocols and procedures enabling device-to-device intercommunication connectivity. This functionality may be provided by incorporating the Bluetooth Intercom Profile® and/or the Bluetooth Telephony Profile®, or other wireless technologies known to those of skill in the art.

This communication may be in accordance with core specifications of one or more subsets of Bluetooth® profiles, wherein the core specifications comprise one or more of: the Cordless Telephony Profile (CTP), the Device ID Profile (DIP), the Dial-up Networking Profile (DUN), the File Transfer Profile (FTP), the Hands-Free Profile (HFP), the Human Interface Device Profile (HID), the Headset Profile (HSP), and the Intercom Profile (ICP), the Proximity Profile (PXP).

Multiple headphones 200 may be networked together and information including media exchanged between them wirelessly. In various embodiments, the media comprises video, audio and/or images. For instance, music stored in computer readable memory on a first pair of headphones 100a may be transmitted using Bluetooth® to one or more other pairs of headphones 100a-z which may themselves be configured to again relay the wireless signal to other interconnected headphones 100. In this manner, a single audio or media file may be instantaneously received by a multitude of headphones wears with each headphone 100 acting both as a receiver, play station, and relay tower in a networked environment.

The headphones 200 may be configured to automatically relay media wireless in response to certain tactile input being received through the touch display 202 which may be specified by the user in the settings, including taping and/or swiping patterns on the touch display 202 or a specific portions of the touch display 202.

Virtual, touch-activated controls may be displayed on the touch display 202 which alternatively may be activated by the user to enable wireless functionality and modified replay of media.

Figure 2B:
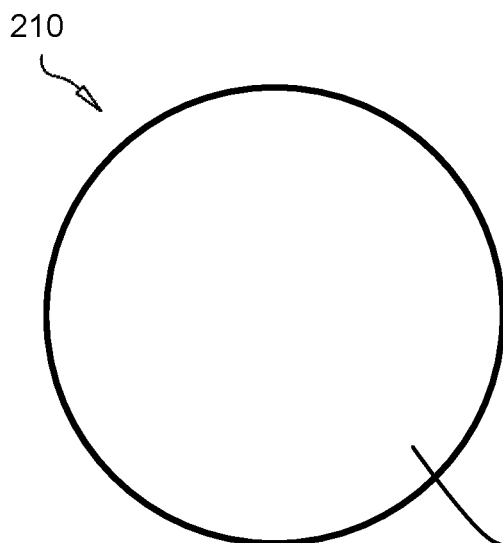
FIG. 2B is a side perspective view of the touch screen of programmable interactive stereo headphones with tap controls and network connectivity in accordance with the present invention.

FIG. 2B is a side perspective view of the programmable interactive stereo headphones with tap controls and network connectivity in accordance with the present invention. In FIG. 2B, the touch display is at rest in the off, or powered off, position. The display is blank.

Figure 2C:
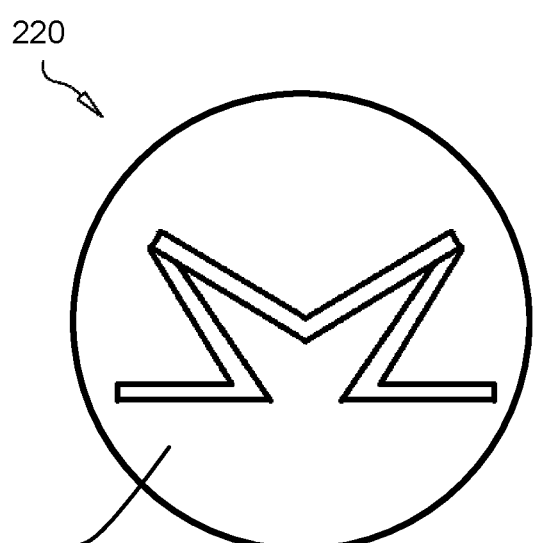
FIG. 2C is a side perspective view of the touch screen of programmable interactive stereo headphones with tap controls and network connectivity in accordance with the present invention.

FIG. 2C is a side perspective view of the touch screen of programmable interactive stereo headphones with tap controls and network connectivity in accordance with the present invention. When the headphones 200 are powered on using the depressible power button 206, a manufacturer's logo 208 is displayed while the headphones 200 are booting up.

In additional embodiments, a wearer may select from a main menu displayed on the touch display 202 after booting up a media file in computer readable member 204 for displaying on the touch display 202. In various embodiments, this media file is an image comprising a logo, colors, or a trademark of another party.

These logos, colors or trademarks may displayed on the headphones 200 as a sign of wearer support for a group, cause, or athletic event. Examples include sporting events at which wearers of the headphones 200 wish to display an image of the logo or mascot of the athletic team the wearer is supporting. In other embodiments, the media file comprises video which is displayed and repeated on the touch display 202. The touch display 202 may be configured by the wearer to display any image exclusively associated with audio being played on the headphones.

Figure 2D:
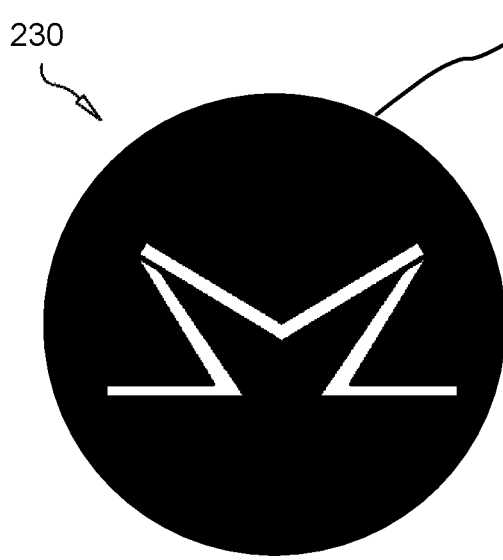
FIG. 2D is a side perspective view of the touch screen of programmable interactive stereo headphones with tap controls and network connectivity in accordance with the present invention.

FIG. 2D is a side perspective view of the programmable interactive stereo headphones with tap controls and network connectivity in accordance with the present invention. The manufacturer's logo 208 may be inverted during boot up, or in low light conditions.

Figure 2E:
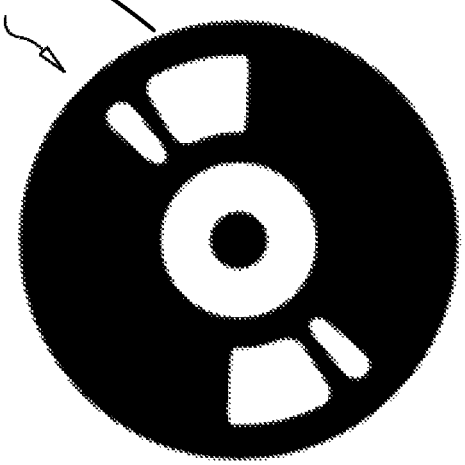
FIG. 2E is a side perspective view of the touch screen of programmable interactive stereo headphones with tap controls and network connectivity in accordance with the present invention.
Figure 2F:
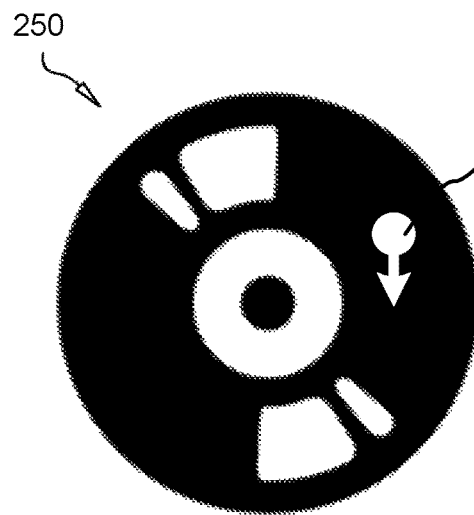
FIG. 2F is a side perspective view of the touch screen of programmable interactive stereo headphones with tap controls and network connectivity in accordance with the present invention.
Figure 2G:
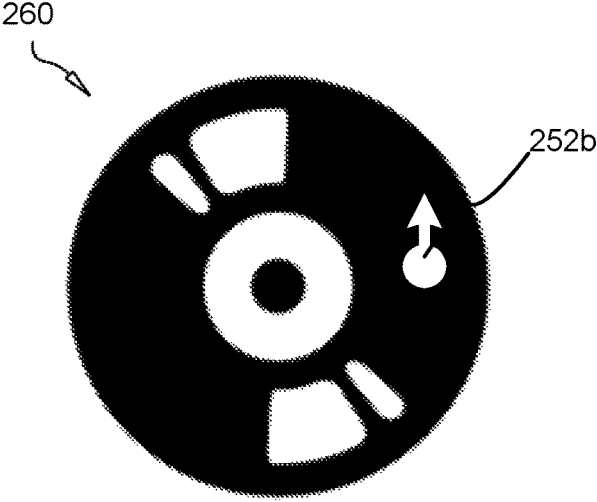
FIG. 2G is a side perspective view of the touch screen of programmable interactive stereo headphones with tap controls and network connectivity in accordance with the present invention.
Figure 2H:
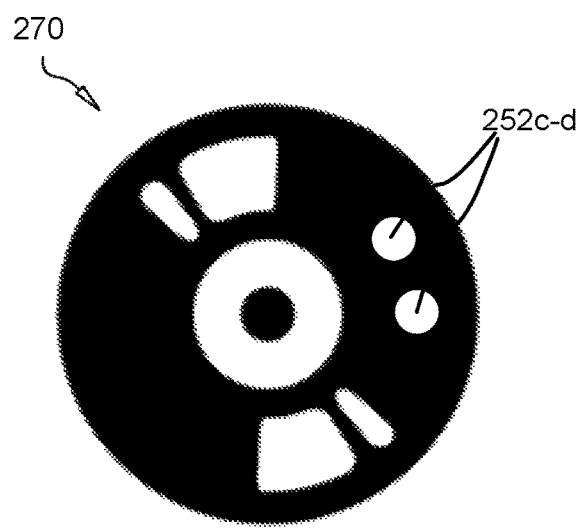
FIG. 2H is a side perspective view of the touch screen of programmable interactive stereo headphones with tap controls and network connectivity in accordance with the present invention.
Figure 2I:
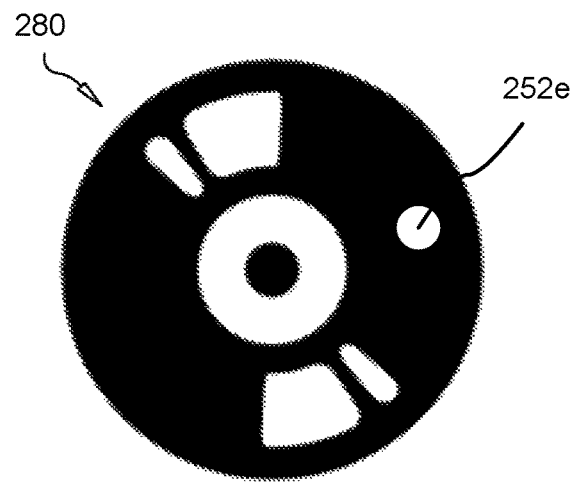
FIG. 2I is a side perspective view of the touch screen of programmable interactive stereo headphones with tap controls and network connectivity in accordance with the present invention.

FIG. 2E is a side perspective view of the programmable interactive stereo headphones with tap controls and network connectivity in accordance with the present invention. As shown, the touch display 202 is configured to display a virtual record.

This virtual record comprises the virtual controls governing playback in some embodiments of the present invention.

FIG. 2F-2I all illustrate a side perspective view of programmable interactive stereo headphones with tap controls and network connectivity in accordance with the present invention. In each of these variations, an environmental touch point 252 is graphically displayed.

The touch display 202 is adapted to sense engagement of a wearer's finger and movement of the finger in a clockwise direction as indicated by the arrow. The headphones 200 are adapted to respond to this movement by fastforwarding the playback of an audio file being played from computer-readable memory 204.

The touch display 202 may be additionally or alternatively adapted to sense engagement of a wearer's finger and movement of the finger in a counterclockwise direction. The headphones 200 are adapted to respond to this movement by rewinding the playback of an audio file being played from computer-readable memory 204.

The touch display 202 may be additionally or alternatively adapted to sense taping of two of the wearer's fingers. The headphones 200 are adapted to respond to this engagement by returning the touch display 202 to a main menu form which the wearer can adjust playback settings, including volume, bass, and maximum volume decibel levels exclusively associated with each speaker in the headphones 200 or alternatively with each earpiece 110.

The touch display 202 may be additionally or alternatively adapted to sense a tap or taping of a user/wearer's finger. The headphones 200 are adapted to respond to this movement by stopping or starting the playback of an audio file being played from computer-readable memory 204.

Figure 2J:
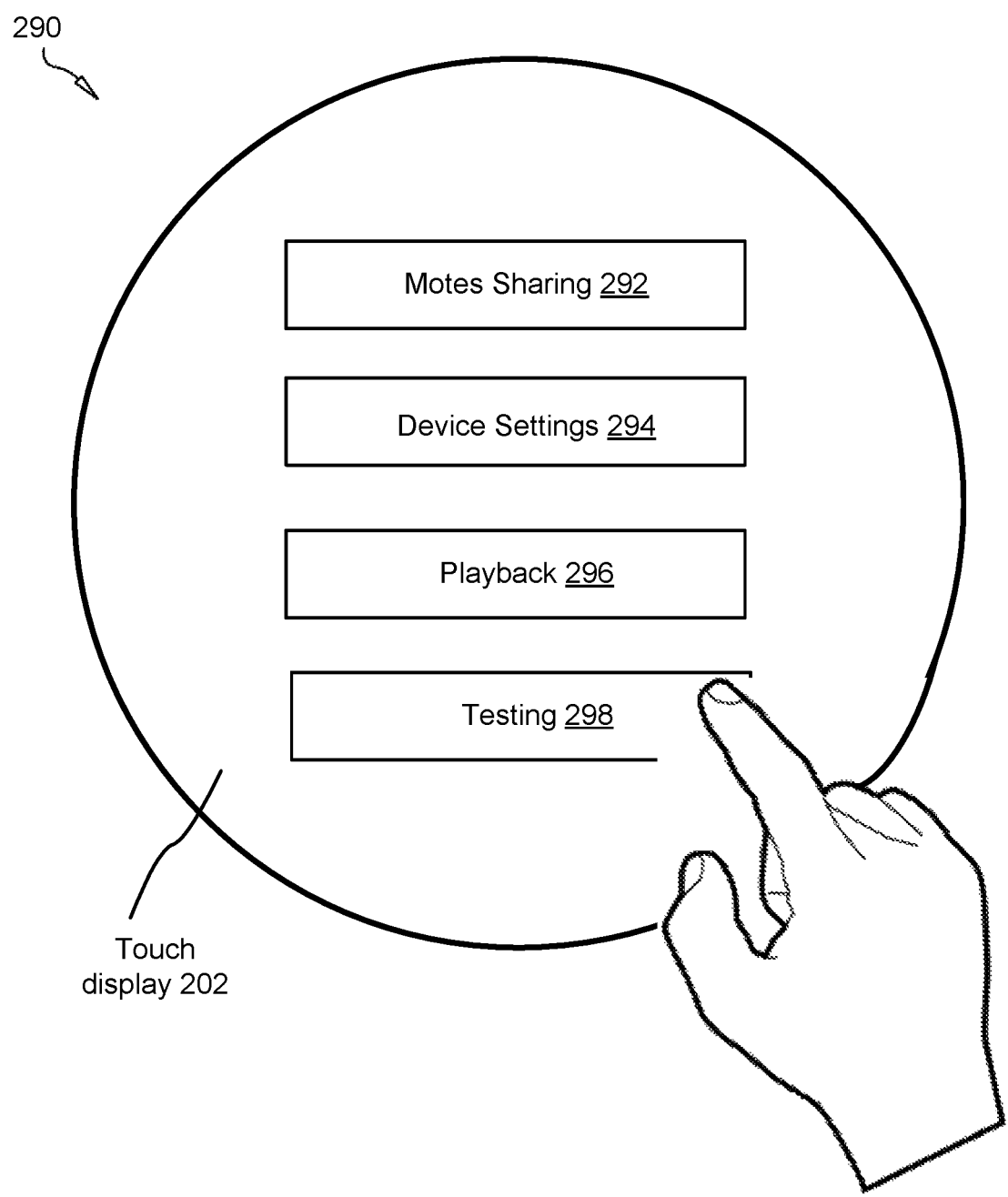
FIG. 2J is a side perspective view of the touch screen of programmable interactive stereo headphones with tap controls and network connectivity in accordance with the present invention.

FIG. 2J is a side perspective view of the touch screen of programmable interactive stereo headphones with tap controls and network connectivity in accordance with the present invention.

Virtual buttons and controls may be displayed on the touch display 202 for facilitating interaction with the wearer or user. In various embodiments, the wearer is prompted to pick from one of a plurality of virtual buttons. In other embodiments, other types of virtual controls are displayed on the touch display 202 including dials, keyboards and meters. A digital keyboard may be displayed to facilitate user entry of a network key, network password, or personal information about the owner of the headphones 100, including name, address, email and telephone number.

Motes sharing 292, when selected, takes a user to a submenu in which functions for receiving and/or sharing media wireless are selectable. Device settings 294, when selected, takes the user to a submenu in which the user can change volume, bass, treble and the like. A playback submenu 296 is accessible via virtual button 296 and testing functions are accessible via testing 298.

Figure 3A:
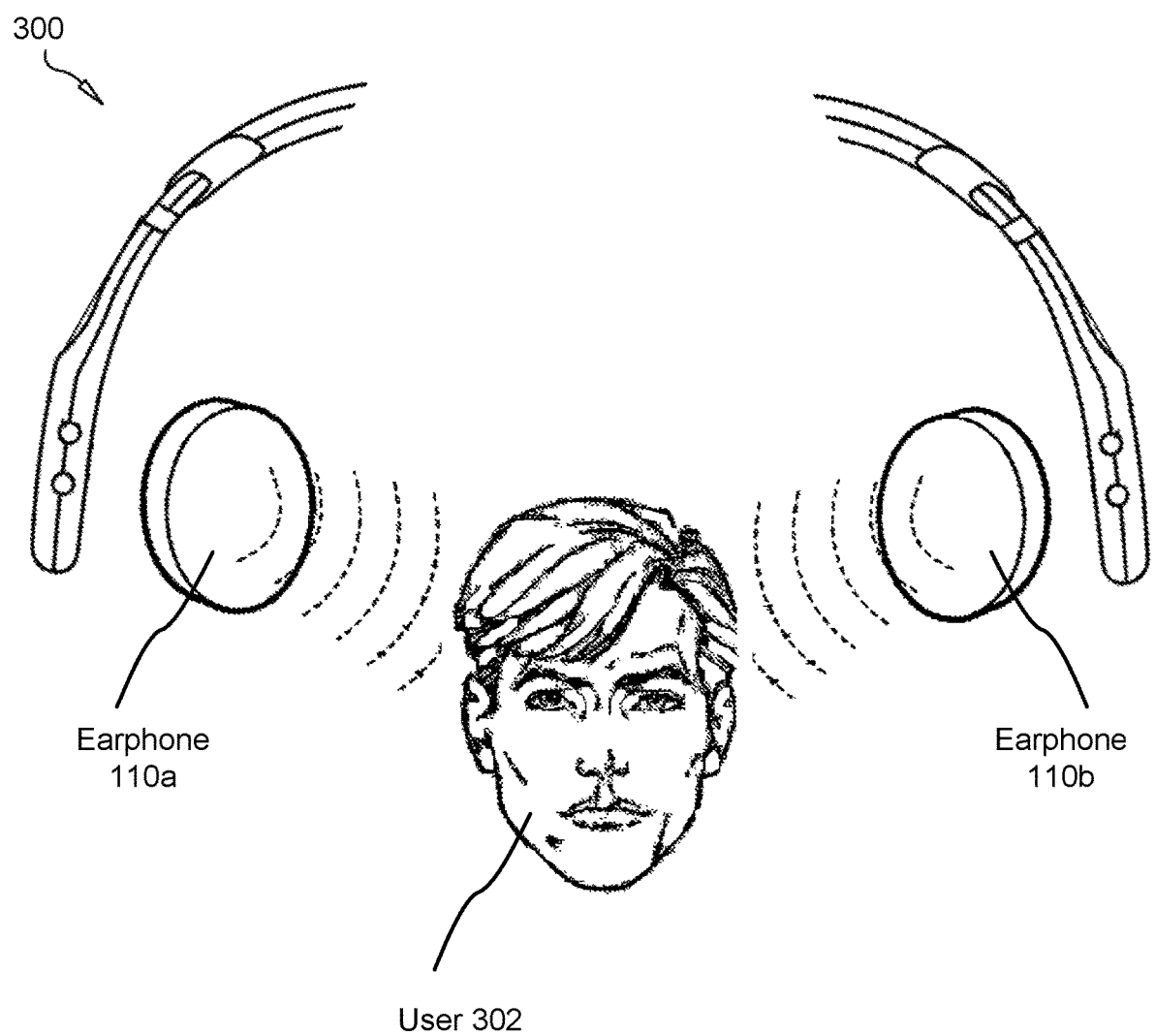
FIG. 3A is a forward perspective view of a headphone of programmable interactive stereo headphones with tap controls and network connectivity in accordance with the present invention.

FIG. 3A is a forward perspective view of a headphone of programmable interactive stereo headphones with tap controls and network connectivity in accordance with the present invention.

Sound emanates to the user 302 from the earphones 110a-b. The volume of each earphone 110a-b may be independently adjusted. Hearing tests are administered through the earphones 110a-b.

Figure 3B:
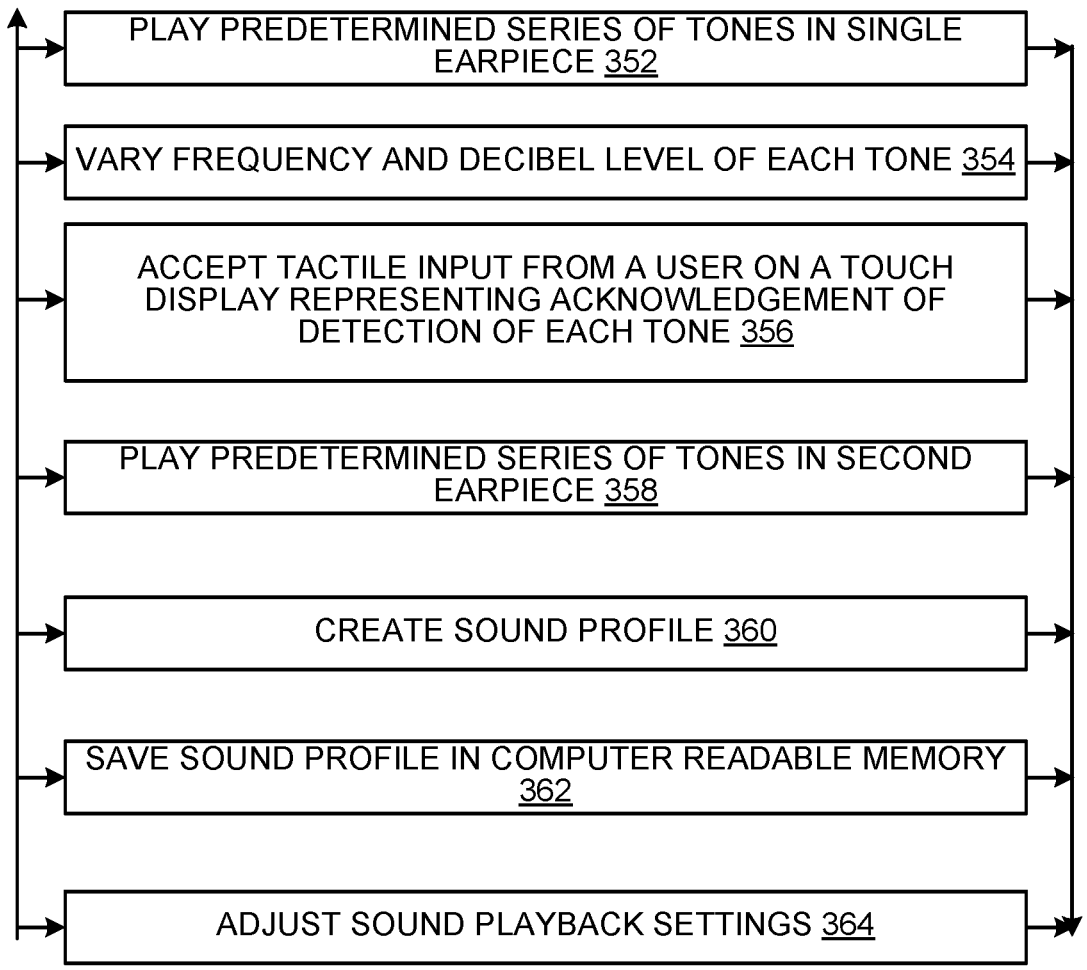
FIG. 3B is a flow chart of a method of screening for hearing loss in accordance with the present invention.

FIG. 3B is a flow chart of a method 350 of screening for hearing loss in accordance with the present invention.

The headphones 100 are adapted to interface with the user primarily through sliding and taping of the user's finger(s) on the touch display 202. Among other features, the headphones 100 are configured and adapted to test hearing loss of user by playing 352 a series of tones across the human hearing spectrum and accepting 356 tactile input from the user. In some embodiments, the user taps the touch display 202 when the user hears the tone. In other embodiments, the user double or triple taps the touch display 202 or slides fingers across the display.

The headphones 100 may gauge hearing loss from age, health, and over exposure to raw sound in high enough decibels to damage hearing. The headphones 100 may be configured to automatically adjust the volume setting for each of the earphones 110 independently in response to the hearing test and in response to determining hearing loss exceeds expectations for the user.

In various embodiments, the headphones 100 execute a hearing screen test (or "hearing test") and audio settings of the headphones 100 are automatically adjusted in computer readable memory in accordance with the results of the hearing test. The headphones may be adapted to test hearing loss in each of a wearer's ears by playing 352 a series of tones as well as to vary 354 the frequencies one at a time in a single earphone (the performing the same test the second earphone) by accepting input from a user in response to the user hearing the predetermined tones, which may vary in their frequency and decibels; by creating 360 a profile of the wearer's hearing sensitivity; and to save the profile in the computer readable memory. The hearing screen test determines both those tones in which a wearer experiences hearing loss, and the degree of loss (or sensitivity to certain predetermined tones).

In response to determining which tones the wearer can hear in each ear, the headphones are configured to amplify sound at frequencies in which a user has hearing loss during media playback after the hearing screen test. In various embodiments, tones a wearer cannot hear are amplified during the hearing screen test to determine the level of hearing loss a wearer has at a given frequency.

The microphone is used to convert sound waves to a digital input which is used by a translation module comprises a computer program product for translating spoken words in once native language into another played through the speakers.

In various other embodiments, the headphones 100 comprise a plurality of microphones for collecting sound surrounding the headphones 100. This ambient sound may be amplified by the headphones 100 and replayed via the speakers for the wearer. In this function, the headphones are used as hearing aids for the wearer. In other embodiments, the microphones are bunched on a forward surface of the headphones 100 to collect sound more effectively emanating towards the front of the headphones 100.

Figure 4:
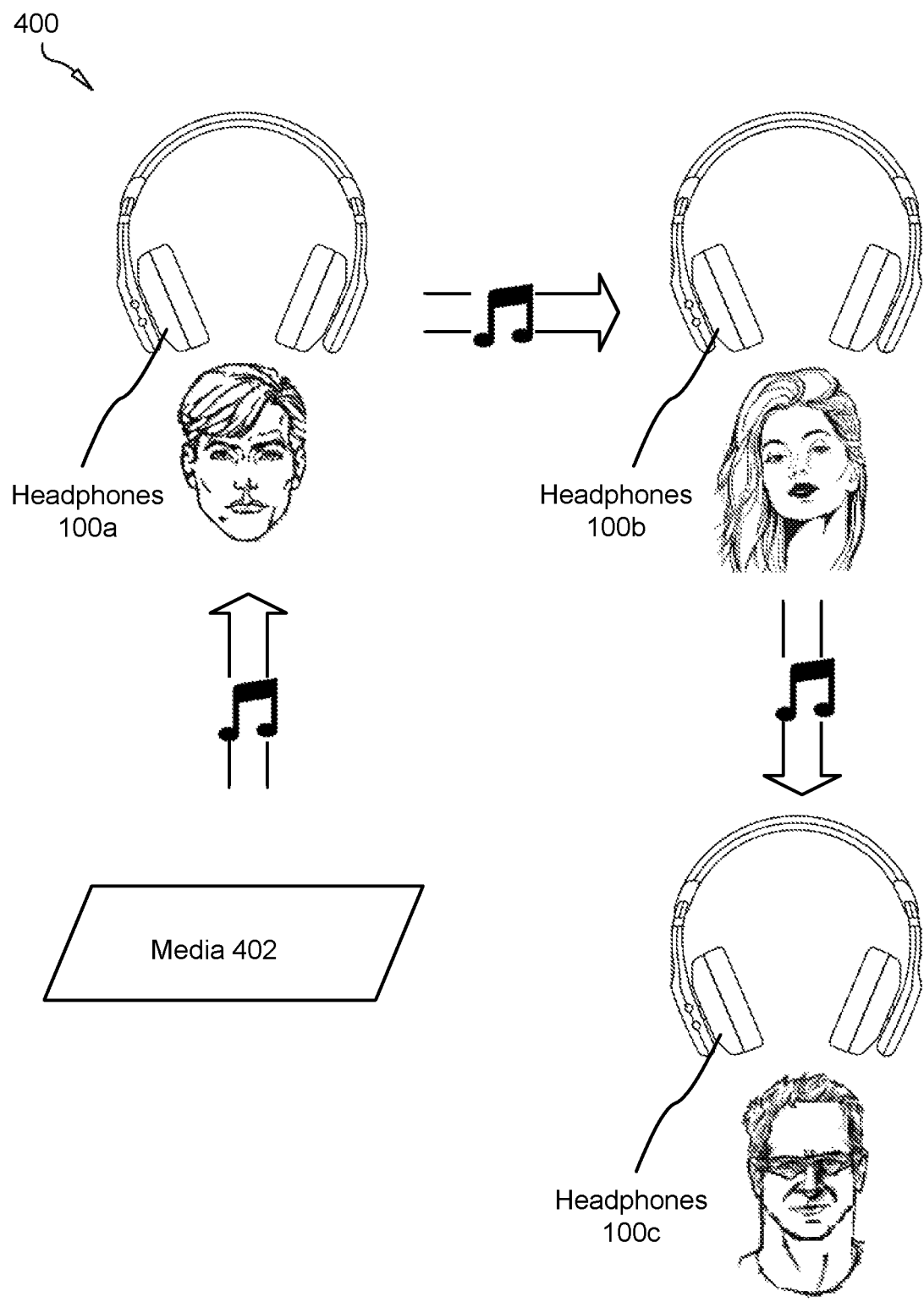
FIG. 4 is a forward perspective view of a series of networked headphones of programmable headphones with virtual controls in accordance with the present invention.

FIG. 4 is a forward perspective view of a series of networked headphones of programmable headphones with virtual controls in accordance with the present invention.

Media is shared between devices 100a-c using means further described above. In the shown embodiment, media 402 is transmitted wirelessly using Bluetooth® or other means known to those of skill in the art.

The media 402 is wireless transmitted to headphones 100a which play the media for a user using predetermined settings. The media 402 is then transmitted from headphones 100a to headphones 100b and replayed, then transmitted from headphones 100b to headphones 100c and likewise replayed.

Figure 5:
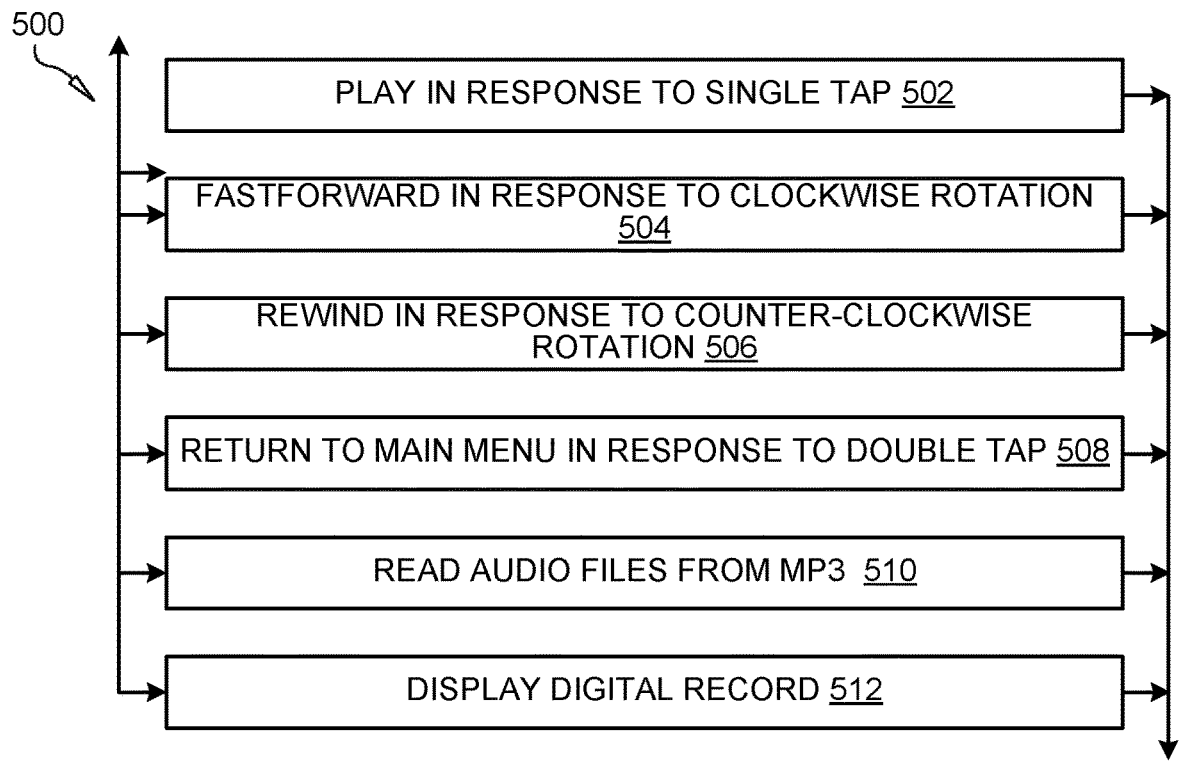
FIG. 5 is a flow chart of the steps of a method for controlling programmable interactive headphones in accordance with the present invention.

FIG. 5 is a flow chart of the steps of a method for controlling programmable interactive headphones in accordance with the present invention.

The method begins 502 when an audio file in memory is played 502 via the headphone 100 is response to a wearer engaging the touch display 202 with a single tap.

The audio file or media 402 is fastforwarded 504 in playback mode in response to a wearer engaging the touch display 202 with a finger in clockwise rotational movement.

The audio file or media 402 is rewound 506 in playback mode in response to a wearer engaging the touch display 202 with a finger in counter-clockwise rotational movement.

The operating system of the headphones 100 reverts or returns 508 to a main menu in response to a wearer engaging the touch display 202 with two fingers simultaneously.

Media 402 or audio files are read 510 from memory, and media in memory may be display 512 on the touch display 202.

Figure 6:
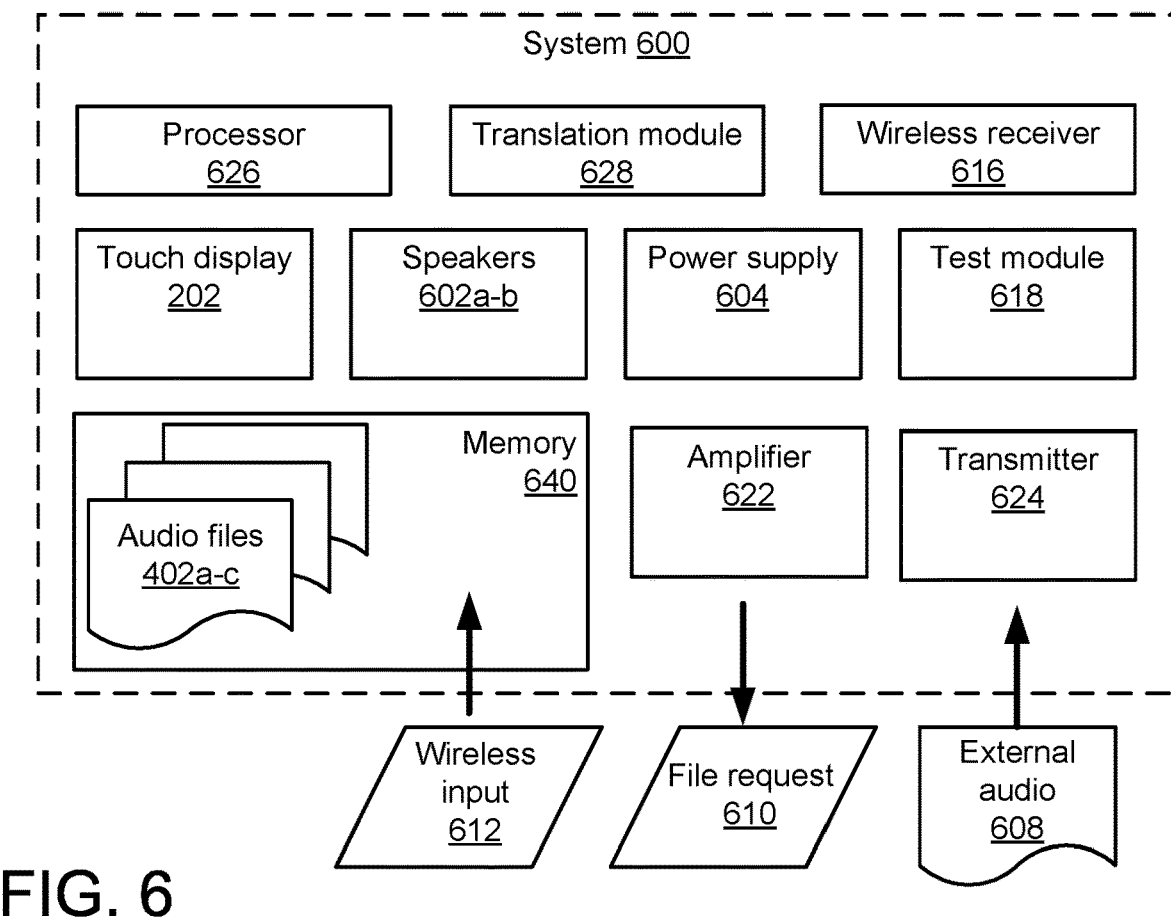
FIG. 6 is a block diagram of the modules of a system for controlling programmable interactive headphones in accordance with the present invention.

FIG. 6 is a block diagram of the modules of a system for controlling programmable interactive headphones in accordance with the present invention.

The system 600 comprises a processor 626, a wireless receiver 616, a touch display 202, speakers 602a-b, a power supply 604, a wireless receiver 616, an advancer module 618, a memory comprising a plurality of audio files 402, an amplifier 622, and a transmitter 624.

In various embodiments, wireless input 612 is received by the system 600 via the receiver 616 using protocols and means known to those of skill in the art, including BlueTooth®. This wireless input 612 may be sent from a remote data processing device (DPD) such as a tablet computer, smart phone, server, personal computer, and the like. In various embodiments, the remote DPD is in wireless connectivity with the system 600 via a local area network (LAN) or wide area network (WAN).

External audio files 608 may be transmitted to the system 600, and the system 600 may alternatively be adapted to transmit file requests 610 to a remote DPD.

In various embodiments, the system 600 comprises a translation module 628 configured to take an audio signal input from the microphone and recognize a spoken language, then translate this spoken language and play the translation via the speakers.

The system 600 may comprise a test module 618 configured to play tones of increasing frequencies and decibels via speakers forming part of the system 600. The test module 618 prompts the wearer to confirm the wearer has heard the sound via the touch display 202 by displaying an virtual acknowledgement button on the display 202.

The test module 618 serves to provide a hearing test to wearers of the headphones 200 or system 600. Wearers may configure the system 600 to play only predetermined tones of specific frequencies and decibels using virtual setting controls on the display 202.

The test module 618 may also be configured to limit audio output by the speakers to 85 decibels or less to protect a wearer's hearing. This 85 decibel level constitutes the predetermined volume threshold; however, the predetermined volume threshold may also be set by a wearer using virtual controls on the touch display 202.

In various embodiments, the system 600 is configured to transmit a digital copy of the audio file 1706 in playback wirelessly to another pair of headphones 100 on a LAN or WAN. In this manner, a plurality of headphones connected on a LAN may simultaneously receive a digital audio signal, which may comprise music, sport commentary, news, or real-time updates.

Using the wireless functionality of the system 600, a system 600a may relay an audio signal to a system 600b, which may in turn relay the same audio signal to a system 600c, and so on, resulting in a plurality of wearers all hearing the same audio input simultaneously. The system 600 may, in this manner, also act as a relay station for wireless signals in large crowds from an initiating source.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. Programmable interactive stereo headphones with tap functionality and network functionality, the headphones comprising:
   an arcuate headband adapted for contouring a wearer's head, the arcuate headband affixed to two earphones;
   two earphones, each earphone comprising a speaker;
   a circular touch screen accessible on an exterior outer surface of the headphones for receiving tactile input from a wearer;
   a battery;
   persistent computer-readable memory insertable and removable from a positioning slot;
   a control module comprising a processor, the control module configured to display virtual controls on the touch display;
   a receiving module configured to receive tactile input on the virtual controls from a user;
   on onboard testing module configured to test hearing loss in each of a wearer's ears by playing a series of tones of predetermines frequencies and decibel levels one at a time in a single earphone; to accept input on the touch display from a user in response to the user hearing the tones; to create an onboard profile of the wearer's hearing sensitivity; to save the onboard profile in the computer readable memory of the headphones; and to amplify tones at which a user experiences hearing loss during media playback based on the onboard profile for the user;
   wherein the control module is configurable by a user to set a maximum volume decibel level for each respective speaker based on both the user's preference and the user's comfort level of sound, the maximum volume decibel level stores in the computer readable memory, whereby an audio output is programmable based on the store maximum volume decibel level based on both the user's preference and the user's comfort level of sound;
   a module configured to relay audio in playback wirelessly to another programmable interactive stereo headphones with tap functionality and network functionality in response to tactile input by the user on a virtual button displayed on the circular touch screen;
   wherein the headphones are adapted to share media wirelessly with one or more separate headphones using Bluetooth® technology.

2. The headphones of claim 1, wherein the virtual controls are manipulable to start, stop, fastforward and rewind playback of an audio file in computer readable memory.

3. The headphones of claim 1, wherein the virtual controls are manipulable using tapping from a user to start, stop, fastforward and rewind playback of an audio file in computer readable memory.

4. The headphones of claim 1, further comprising a plurality of depressible buttons for raising and lower a volume of sound emanating from the speakers.

5. The headphones of claim 1, wherein the control module is configurable by a user to set a maximum volume decibel level for each respective speaker, the maximum volume decibel level stored in the computer readable memory.

6. The headphones of claim 1, wherein the control module limits sounds emitting from each speaker to a volume less than the maximum volume decibel level exclusively associated with said speaker.

7. The headphones of claim 1, wherein the touch screen is adapted to fast forward playback of an audio file in computer-readable memory in response to sensing a wearer's engagement of the touch screen with a finger in a clockwise direction.

8. The headphones of claim 7, wherein the touch screen is adapted to rewind playback of an audio file in computer-readable memory in response to sensing a wearer's engagement of the touch screen with a finger in a counterclockwise direction.

9. The headphones of claim 8, wherein the touch screen is adapted to stop forward playback of an audio file in computer-readable memory in response to sensing a wearer's tapping the touch screen with two fingers.

10. The headphones of claim 9, wherein the touch screen is adapted to return to a main menu in response to sensing a wearer's tapping the touch screen with two fingers.

11. The headphones of claim 1, further comprising a wireless receiver, the headphones adapted to receive wireless input via the wireless receiver transmitted from a tablet computer, the wireless input changing playback settings on the headphones.

12. The headphones of claim 11, wherein an output of the speakers is limited to 85 decibels.

13. The headphones of claim 1, wherein the touch screen is configured by the wearer to display an image exclusively associated with audio being played on the headphones.

14. The headphones of claim 1, wherein an audio file being played back on the headphones is transmitted wireless to a second pair of headphones connected with the headphones via a Local Area Network (LAN).

15. The headphones of claim 1, further comprising a plurality of forward-facing cameras adapted for use in different lighting conditions.

* * * * *